(12) United States Patent
Kashiwada et al.

(10) Patent No.: US 11,543,420 B2
(45) Date of Patent: Jan. 3, 2023

(54) BLOOD CLOTTING TIME MEASUREMENT CARTRIDGE AND BLOOD CLOTTING TIME MEASURING DEVICE

(71) Applicant: APEL CO., LTD, Kawaguchi (JP)

(72) Inventors: Minoru Kashiwada, Kawaguchi (JP);
Mitsuru Kashiwada, Kawaguchi (JP);
Akira Takayama, Kawaguchi (JP);
Yasuichi Haga, Kawaguchi (JP)

(73) Assignee: APEL CO., LTD, Kawaguchi (JP)

( * ) Notice: Subject to any disclaimer, the term of this patent is extended or adjusted under 35 U.S.C. 154(b) by 392 days.

(21) Appl. No.: 16/649,000

(22) PCT Filed: Dec. 28, 2018

(86) PCT No.: PCT/JP2018/048528
§ 371 (c)(1),
(2) Date: Mar. 19, 2020

(87) PCT Pub. No.: WO2019/142650
PCT Pub. Date: Jul. 25, 2019

(65) Prior Publication Data
US 2020/0292563 A1    Sep. 17, 2020

(30) Foreign Application Priority Data

Jan. 16, 2018  (JP) .............................. JP2018-004698
May 24, 2018  (JP) .............................. JP2018-100060
Jul. 26, 2018  (JP) .............................. JP2018-140407

(51) Int. Cl.
*B01L 3/00*      (2006.01)
*G01N 33/86*     (2006.01)

(52) U.S. Cl.
CPC .......... *G01N 33/86* (2013.01); *B01L 3/50273* (2013.01); *B01L 3/502715* (2013.01);
(Continued)

(58) Field of Classification Search
CPC ........ G01N 33/86; G01N 33/50; G01N 33/48; G01N 33/00; G01N 33/54388;
(Continued)

(56) References Cited

U.S. PATENT DOCUMENTS 5,372,946 A      12/1994  Cusak et al.
5,504,011 A  *    4/1996  Gavin ................... G01N 33/86
                                                        600/576
(Continued)

FOREIGN PATENT DOCUMENTS

CN    100371065 C     2/2008
CN    102215965 A    10/2011
(Continued)

OTHER PUBLICATIONS

Kashiwada Minoru, JP 2015 206608 English Machine Translation of Description, obtained from espacenet.com, Jun. 10, 2022, p. 1-26. (Year: 2022).*

(Continued)

*Primary Examiner* — Christine T Mui
(74) *Attorney, Agent, or Firm* — Oliff PLC

(57) ABSTRACT

A blood clotting time measurement cartridge includes: an inlet on one end of a measurement flow channel and through which blood is introduced; a communication opening on the other end of the measurement flow channel and through which air suction or air pressure application or the blood introduced from the inlet is performed; a moving body arranged in the measurement flow channel moves; a clotting accelerator applied on at least one of a flow channel wall surface, which defines the measurement flow channel, and the moving body; and a detection area through which light is transmitted to a predetermined part in the measurement flow channel, and where it is possible to detect with light whether there is the moving body or the blood making a (Continued)

reciprocating motion in the measurement flow channel in association with air suction or air pressure application or the blood from the communication opening.

15 Claims, 10 Drawing Sheets

(52) U.S. Cl.
CPC ..... *B01L 2300/047* (2013.01); *B01L 2300/06* (2013.01); *B01L 2300/0861* (2013.01); *B01L 2400/049* (2013.01)

(58) Field of Classification Search
CPC ....... G01N 33/54386; G01N 33/54366; G01N 33/543; G01N 33/53; B01L 3/502715; B01L 3/50273; B01L 2300/047; B01L 2300/06; B01L 2300/0861; B01L 2400/049
USPC ............................................. 600/369; 422/50
See application file for complete search history.

(56) References Cited

U.S. PATENT DOCUMENTS

| | | | |
|---|---|---|---|
| 2009/0247902 | A1 | 10/2009 | Reichert et al. |
| 2016/0038939 | A1 | 2/2016 | Min et al. |

FOREIGN PATENT DOCUMENTS

| | | |
|---|---|---|
| CN | 112673260 A | 4/2021 |
| JP | S55-153133 U | 11/1980 |
| JP | H03-500573 A | 2/1991 |
| JP | H11-514087 A | 11/1999 |
| JP | 2002-214241 A | 7/2002 |
| JP | 2005-046652 A | 2/2005 |
| JP | 2006-234590 A | 9/2006 |
| JP | 2009-279507 A | 12/2009 |
| JP | 2010-025645 A | 2/2010 |
| JP | 2010-078608 A | 4/2010 |
| JP | 2010-243419 A | 10/2010 |
| JP | 2011-050936 A | 3/2011 |
| JP | 2012-508879 A | 4/2012 |
| JP | 2014-044103 A | 3/2014 |
| JP | 2014-521954 A | 8/2014 |
| JP | 2014-198324 A | 10/2014 |
| JP | 2015-510111 A | 4/2015 |
| JP | 2015-200612 A | 11/2015 |
| JP | 2015-206608 A | 11/2015 |
| JP | 2016-520824 A | 7/2016 |
| JP | 2016-180640 A | 10/2016 |
| JP | 6415775 B1 | 10/2018 |
| JP | 2019-124548 A | 7/2019 |
| JP | 2019-203827 A | 11/2019 |
| JP | 2019-203872 A | 11/2019 |
| TW | 201331582 A | 8/2013 |
| TW | M533212 U | 12/2016 |
| TW | 201932836 A | 8/2019 |
| WO | 97/046887 A1 | 12/1997 |
| WO | 2008/072870 A1 | 6/2008 |
| WO | 2009/069656 A1 | 6/2009 |
| WO | 2010/056185 A1 | 5/2010 |
| WO | 2011/105596 A1 | 9/2011 |
| WO | 2013/015822 A1 | 1/2013 |
| WO | 2015/019626 A1 | 2/2015 |
| WO | 2019/142650 A1 | 7/2019 |

OTHER PUBLICATIONS

Yonetani Akira, JP 2011-050936 A English Machine Translation of Description, obtained on Jun. 10, 2022, p. 1-29. (Year: 2022).*
Mar. 26, 2019 Search Report issued in International Patent Application No. PCT/JP2018/048528.
Jul. 10, 2018 Office Action issued in Japanese Patent Application No. 2018-100060.
Aug. 28, 2018 Notice of Allowance issued in Japanese Patent Application No. 2018-100060.
Aug. 2, 2018 Office Action issued in Japanese Patent Application No. 2018-004698.
Oct. 23, 2018 Office Action issued in Japanese Patent Application No. 2018-004698.
Dec. 4, 2018 Notice of Allowance issued in Japanese Patent Application No. 2018-004698.
Sep. 25, 2018 Notice of Allowance issued in Japanese Patent Application No. 2018-140407.
Oct. 7, 2019 Office Action issued in Taiwanese Patent Application No. 108101409.
Feb. 5, 2020 Notice of Allowance issued in Taiwanese Patent Application No. 108101409.
Oct. 27, 2020 International Search Report issued in International Patent Application No. PCT/JP2020/033041.
Nov. 26, 2019 Office Action issued in Japanese Patent Application No. 2019-164197.
Jan. 22, 2020 Written Amendment submitted in Japanese Patent Application No. 2019-164197.
Mar. 10, 2020 Office Action issued in Japanese Patent Application No. 2019-164197.
Apr. 2, 2020 Written Amendment submitted in Japanese Patent Application No. 2019-164197.
Jun. 30, 2020 Office Action issued in Japanese Patent Application No. 2019-164197.
Jul. 15, 2020 Written Amendment submitted in Japanese Patent Application No. 2019-164197.
Aug. 18, 2020 Notice of Allowance issued in Japanese Patent Application No. 2019-164197.
Dec. 1, 2020 Notice of Allowance issued in Taiwanese Patent Application No. 109130675.
U.S. Appl. No. 17/260,487, filed Jan. 14, 2021.
Oct. 9, 2021 Office Action issued in Chinese Patent Application No. 202110117155.3.
Jan. 10, 2022 Response filed in Chinese Patent Application No. 202110117155.3.
Jan. 26, 2022 Office Action issued in Chinese Patent Application No. 202080003234.5.
Jul. 5, 2021 Office Action issued in Chinese Patent Application No. 202080003234.5.
Oct. 12, 2021 Response filed in Chinese Patent Application No. 202080003234.5.
Jun. 2, 2020 Office Action issued in Taiwanese Patent Application No. 108147224.
Aug. 6, 2020 Notice of Allowance issued in Taiwanese Patent Application No. 108147224.
Nov. 30, 2020 Office Action issued in Chinese Patent Application No. 201880028634.4.
Feb. 5, 2021 Statement of Opinion and Amendment submitted in Chinese Patent Application No. 201880028634.4.
Chinese Divisional Application No. 202110117155.3 filed Jan. 28, 2021.

* cited by examiner (a)

(b)

BLOOD CLOTTING TIME MEASUREMENT CARTRIDGE AND BLOOD CLOTTING TIME MEASURING DEVICE

TECHNICAL FIELD

The present invention relates to a blood clotting time measurement cartridge used in measurement of time until blood is clotted, and a blood clotting time measuring device that uses this blood clotting time measurement cartridge.

BACKGROUND ART

In a case where extracorporeal circulation such as dialysis or an artificial heart-lung machine used in a surgery of a circulatory system is performed, or a case where treatment of a cardiac catheter is performed, anticoagulant such as heparin is used to prevent clotting of blood. It is important to use an appropriate amount of such anticoagulant since there is a case where an extracorporeal circulation path is occluded when a dosage amount thereof is not enough, and stopping bleeding becomes difficult when a dosage amount thereof is too much. Conventionally, in such a case, for example, a method of determining a dosage amount or time of dosing of a clotting accelerator by accelerating clotting of blood by mixing of a clotting accelerator into the blood, and measuring time of determination that a predetermined percentage of the blood is clotted (clotting time of blood) is employed, and various technologies for that have been proposed.

For example, in Patent Literature 1, a technology in which a measurement cartridge including a forked capillary tube having a narrowed part, and a measuring device including an air pump are included, the air pump is connected to each capillary tube by setting of the cartridge to the measuring device, clotting of blood put into the capillary tube is accelerated in a narrowed part by a reciprocating motion with the air pump, and clotting time of the blood is measured from a variation in time necessary for this reciprocating motion is disclosed.

Also, in Patent Literature 2, a technology in which a measurement cartridge in which a spherical object is arranged in a measurement flow channel, and a measuring device that can oscillate the set measurement cartridge are included, the spherical object is made to make a reciprocating motion in the measurement flow channel along with blood in association with oscillation of the cartridge, anticoagulant previously applied on the measurement flow channel is dissolved and clotting is accelerated thereby, and clotting time of the blood is measured from a variation in time that is necessary for the reciprocating motion of the blood and that is measured at the time is disclosed.

CITATION LIST

Patent Literature

Patent Literature 1: U.S. Pat. No. 5,372,946
Patent Literature 2: JP 2015-200612 A

SUMMARY OF INVENTION

Technical Problem

Incidentally, high dimensional accuracy is required in a flow channel in which blood moves in such a measurement cartridge since clotting time is influenced when there is a variation in a form or a size. Thus, a cost is increased. Here, as described above, a capillary tube is forked and has a long length, a cost of the measurement cartridge in the Patent Literature 1 is increased for that. In addition, since it is necessary to completely transmit pressure from an air pump to a capillary tube, in performance, in order to connect the air pump to the capillary tube, it is necessary to air-tightly connect the air pump and the capillary tube. Thus, high dimensional accuracy is required for a connection part in each of the measuring device and the measurement cartridge. This spurs an increase in a cost. Also, since it is necessary to employ, as an air pump, something like a micropump that can accurately control a small amount of air, a cost is further increased.

On the other hand, a measurement cartridge in Patent Literature 2 can be formed relatively easily since only one measurement flow channel is provided linearly. However, since an oscillating mechanism needs to be provided in a measuring device, there is still a room for improvement as a whole in a cost reduction.

Also, in order to accelerate clotting of blood and precisely measure clotting time in a shorter period in such a measurement cartridge, it is preferable to stir the blood efficiently. Here, in the cartridge in Patent Literature 1, a direction of a flow is switched by a reciprocating motion of blood and a speed or the like of the flow is changed by passage through a narrowed part, whereby the blood is stirred. However, a cartridge that can more efficiently and securely stir blood and can measure clotting time of the blood precisely in a shorter period is demanded.

The present invention is to solve such a problem and to provide a blood clotting time measurement cartridge which has a relatively simple structure and a cost of which can be controlled, and a blood clotting time measuring device that uses this blood clotting time measurement cartridge. Also, a different purpose of the present invention is to provide a blood clotting time measurement cartridge with which blood can be efficiently stirred and clotting time can be precisely measured in a shorter period, and a blood clotting time measuring device that uses this blood clotting time measurement cartridge.

Solution to Problem

The present invention is a blood clotting time measurement cartridge including: a measurement flow channel extended long with respect to a cross-sectional area; an inlet which is provided on one end side of the measurement flow channel and through which blood can be introduced; a communication opening which is provided on the other end side of the measurement flow channel and through which suction or pressure application with respect to air in the measurement flow channel or the blood introduced from the inlet into the measurement flow channel can be performed; a moving body that is arranged in the measurement flow channel and that can move in the measurement flow channel; a clotting accelerator applied on at least one of a flow channel wall surface, which defines the measurement flow channel, and the moving body; and a detection area through which light can be transmitted with respect to a predetermined part in the measurement flow channel and in which it can be detected with light whether there is, in the predetermined part, the moving body or the blood making a reciprocating motion in the measurement flow channel in association with suction or pressure application of the air or the blood from the communication opening, wherein an air chamber connected to the communication opening, and a diaphragm that closes the air chamber, and makes the moving body and the blood make the reciprocating motion by applying pressure or reducing pressure with respect to the air chamber are included, and the diaphragm is sandwiched between a cylindrical wall which has a cylindrical shape and an inner space of which is the air chamber, and a holder that has an annular shape and that is inserted into the cylindrical wall on an outer side in a radial direction of the cylindrical wall.

In such a blood clotting time measurement cartridge, the measurement flow channel preferably includes a narrowed part in a vicinity of the detection area.

Also, a shielding part that prevents blood from flowing toward the detection area is preferably included on an outer side of the inlet.

Also, the present invention is a blood clotting time measurement cartridge including: a measurement flow channel extended long with respect to a cross-sectional area; an inlet which is provided on one end side of the measurement flow channel and through which blood can be introduced; a communication opening which is provided on the other end side of the measurement flow channel and through which suction or pressure application with respect to air in the measurement flow channel or the blood introduced from the inlet into the measurement flow channel can be performed; a storage chamber that is connected to the communication opening and that stores the blood flowing out of the communication opening; a stirring bar that is arranged in the storage chamber and that stirs the blood in the storage chamber; a clotting accelerator applied on at least one of a flow channel wall surface that defines the measurement flow channel, a storage chamber wall surface that defines the storage chamber, and the stirring bar; and a detection area through which light can be transmitted with respect to a predetermined part in the measurement flow channel and in which it can be detected with light whether there is, in the predetermined part, the blood making a reciprocating motion in the measurement flow channel in association with suction or pressure application of the air or the blood from the communication opening.

Here, the measurement flow channel preferably includes a narrowed part in a vicinity of the detection area.

Also, a shielding part that prevents blood from flowing toward the detection area is preferably included on an outer side of the inlet.

Moreover, an air chamber connected to the storage chamber, and a diaphragm that closes the air chamber and makes the blood make a reciprocating motion in the measurement flow channel by applying pressure or reducing pressure with respect to the air chamber are preferably included.

Then, in a blood clotting time measuring device to which the above-described blood clotting time measurement cartridge is set, a detection means that is provided in a position corresponding to the detection area and that can detect the moving body or the blood with light, and a pressing means that can push or pull the diaphragm for a predetermined moving amount are preferably included.

The present invention is a blood clotting time measurement cartridge including: a measurement flow channel in which blood is housed; an inlet which is provided on one end side of the measurement flow channel and through which the blood is introduced into the measurement flow channel; a communication opening which is provided on the other end side of the measurement flow channel and through which suction or pressure application with respect to air in the measurement flow channel or the blood introduced from the inlet into the measurement flow channel can be performed; and a detection area through which light can be transmitted with respect to a predetermined part in the measurement flow channel and in which it is detected with light whether there is, in the predetermined part, the blood making a reciprocating motion in the measurement flow channel in association with suction or pressure application of the air or the blood in the measurement flow channel from the communication opening, wherein the measurement flow channel includes a helical flow channel in at least a part thereof, the helical flow channel is defined between a wall surface of a groove part that connects the inlet and the communication opening, and an outer peripheral surface of a shaft-like member that is housed in the groove part and that has a helical groove part winding in a helical manner in a surface, and the groove part has a pair of protruded parts that forms a narrowed part, in which the measurement flow channel is narrowed down, by being protruded from the wall surface of the groove part and that is placed in a vicinity of the detection area with the shaft-like member therebetween.

Here, at least one of the protruded parts preferably has an inclination surface on an opposite side of a side facing the shaft-like member.

Also, the present invention is a blood clotting time measuring device to which the above-described blood clotting time measurement cartridge is set, and includes a detection means that is provided in a position corresponding to the detection area and that can detect the blood with light.

Advantageous Effects of Invention

In a blood clotting time measurement cartridge of the present invention, a measurement flow channel in which blood moves can be formed relatively easily since being a single flow channel extended long with respect to a cross-sectional area. Also, a cost can be controlled since clotting time of blood is measured by suction or pressure application of air or blood in a measurement flow channel without an oscillating mechanism in a manner of Patent Literature 2.

Then, in what includes a moving body in a measurement flow channel, it is possible to stir blood by a reciprocating motion of the moving body in the measurement flow channel. Thus, it is possible to efficiently and stably dissolve, into the blood, a clotting accelerator applied on at least one of a flow channel wall surface, which defines the measurement flow channel, and the moving body. That is, since it is possible to control a variation in dissolving of a clotting accelerator in blood, an error factor in clotting time is removed and measurement of the clotting time can be performed stably. Also, since a minute gap through which blood can pass is formed between an outer peripheral surface of the moving body and an inner peripheral surface of the measurement flow channel, movement of the moving body becomes slow when clotting of the blood is started in this gap and a cycle of a reciprocating motion of the moving body becomes long compared to a state in which the blood is not clotted. Thus, it is possible to obtain clotting time of the blood from this difference in a cycle. Also, in a case where a moving body is provided, by providing a detection area through which light can be transmitted to a predetermined part in a measurement flow channel, it is possible to detect whether there is the moving body making a reciprocating motion in this predetermined part. Note that in this detection area, blood making a reciprocating motion along with the moving body may be detected.

Also, in what includes a stirring bar in a storage chamber, it is possible to efficiently dissolve, into blood, a clotting accelerator applied on at least one of a flow channel wall surface that defines a measurement flow channel, a storage chamber wall surface that defines a storage chamber, and a stirring bar. That is, in this case, a variation in dissolving of a clotting accelerator into blood is also controlled. Thus, an error factor in clotting time is removed and the clotting time can be measured stably.

Then, in a case where a narrowed part is included in a vicinity of a detection area in the measurement flow channel, clotted blood or a moving body to which the clotted blood is attached becomes likely to be stuck in the narrowed part. Thus, it is possible to stably detect the blood and the moving body in the detection area.

Then, what includes a moving body is configured in such a manner as to include an air chamber connected to a communication opening, and a diaphragm that closes the air chamber and makes the moving body make a reciprocating motion by applying pressure or reducing pressure in this air chamber. Also, what includes a stirring bar is configured in such a manner as to include an air chamber connected to a storage chamber, and a diaphragm that closes the air chamber and that makes blood make a reciprocating motion in a measurement flow channel by applying pressure or reducing pressure in this air chamber. Thus, a connection part that has to connect an air pump and a capillary tube air-tightly in a manner of Patent Literature 1 becomes unnecessary, and a cost can be controlled. Also, in a blood clotting time measuring device to which a blood clotting time measurement cartridge of the present invention is attached, it is possible to adjust pressure in an air chamber by changing a pushing amount into a diaphragm. Thus, it is not necessary to use an expensive micropump in a manner of Patent Literature 1, and a cost can be also reduced in this point.

Also, in a case where a shielding part to prevent blood from flowing toward a detection area is provided on an outer side of an inlet, the blood does not flow into the detection area due to the shielding part even when the blood is spilt in injection of the blood into the inlet. Thus, a trouble such as that measurement of clotting time is interrupted or that it becomes impossible to use a cartridge due to the spilt blood is not generated.

Also, in a blood clotting time measurement cartridge of the present invention, in a case where a helical flow channel is included in at least a part of a measurement flow channel in which blood is housed, it is possible to efficiently and securely stir the blood by making the blood pass through the helical flow channel. Thus, it is possible to precisely measure clotting time of the blood in a shorter period. Also, with the helical flow channel, an effect that a flow channel length of the measurement flow channel can be made longer without a change in a length in a longitudinal direction of the cartridge is acquired (effect that length in longitudinal direction of cartridge can be made shorter while flow channel length of measurement flow channel is kept may be acquired, or both effect can be combined).

A helical flow channel can be formed with various configurations. In a case where a groove part connecting an inlet and the communication opening, and a shaft-like member that is housed in this groove part and that includes a helical groove part winding in a helical manner in a surface are included, and a helical flow channel is defined between a wall surface of the groove part and an outer peripheral surface of the shaft-like member, a configuration can be more simple and inexpensive. Also, in order to detect clotting of blood, it is preferable to narrow down a height and a width of a path of a helical flow channel in such a manner that it becomes difficult for the blood that starts to be clotted and that has increased viscosity to pass through.

When a configuration of arranging a shaft-like member in a groove part in such a manner is employed, it is possible to narrow down a height and a width of a path of a rotation-shaped flow channel at high dimensional accuracy. Thus, it is possible to more quickly and stably perform measurement of clotting time of the blood.

Also, in a case where a pair of protruded parts that is protruded from a wall surface of a groove part, that sandwiches a shaft-like member therebetween, and that is placed in a vicinity of a detection area is provided in the groove part, it is possible to house the shaft-like member in a predetermined position. Also, since it becomes difficult for blood with increased viscosity to pass through a part in which a measurement flow channel is narrowed down by the protruded parts (narrowed part), it is possible to stably detect existence/non-existence of blood in the detection area. Then, in a case where an inclination surface is provided on an opposite side of a side facing the shaft-like member in at least one of the protruded parts, it becomes unlikely to involve an air bubble when blood passes through the narrowed part. Thus, erroneous detection due to the air bubble is controlled, and accuracy of detecting existence/non-existence of the blood in the detection area can be stabilized more.

DESCRIPTION OF EMBODIMENTS

Figure 1:
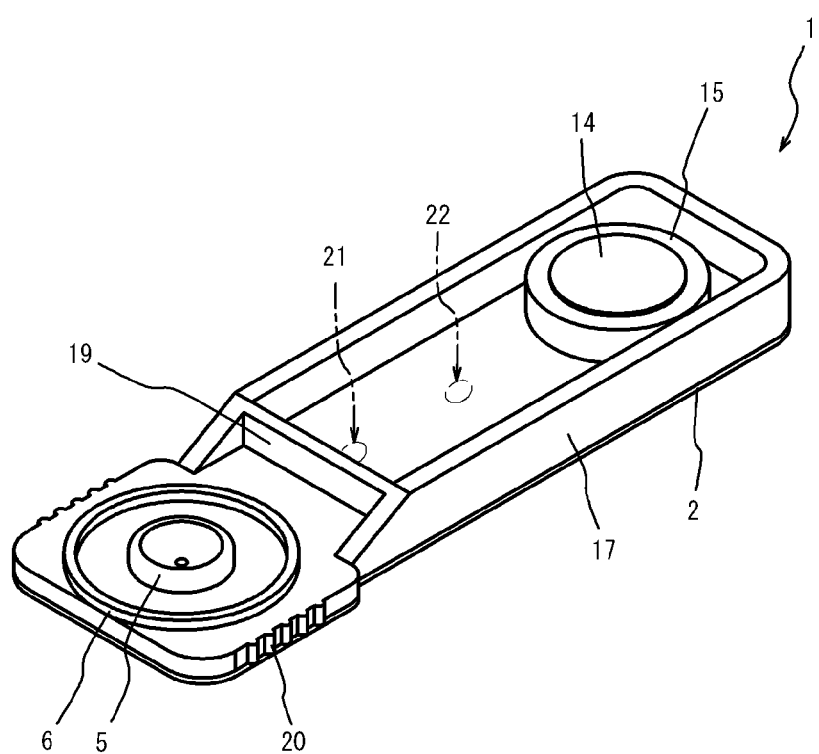
FIG. 1 is a perspective view illustrating a first embodiment of a blood clotting time measurement cartridge according to the present invention.
Figure 2:
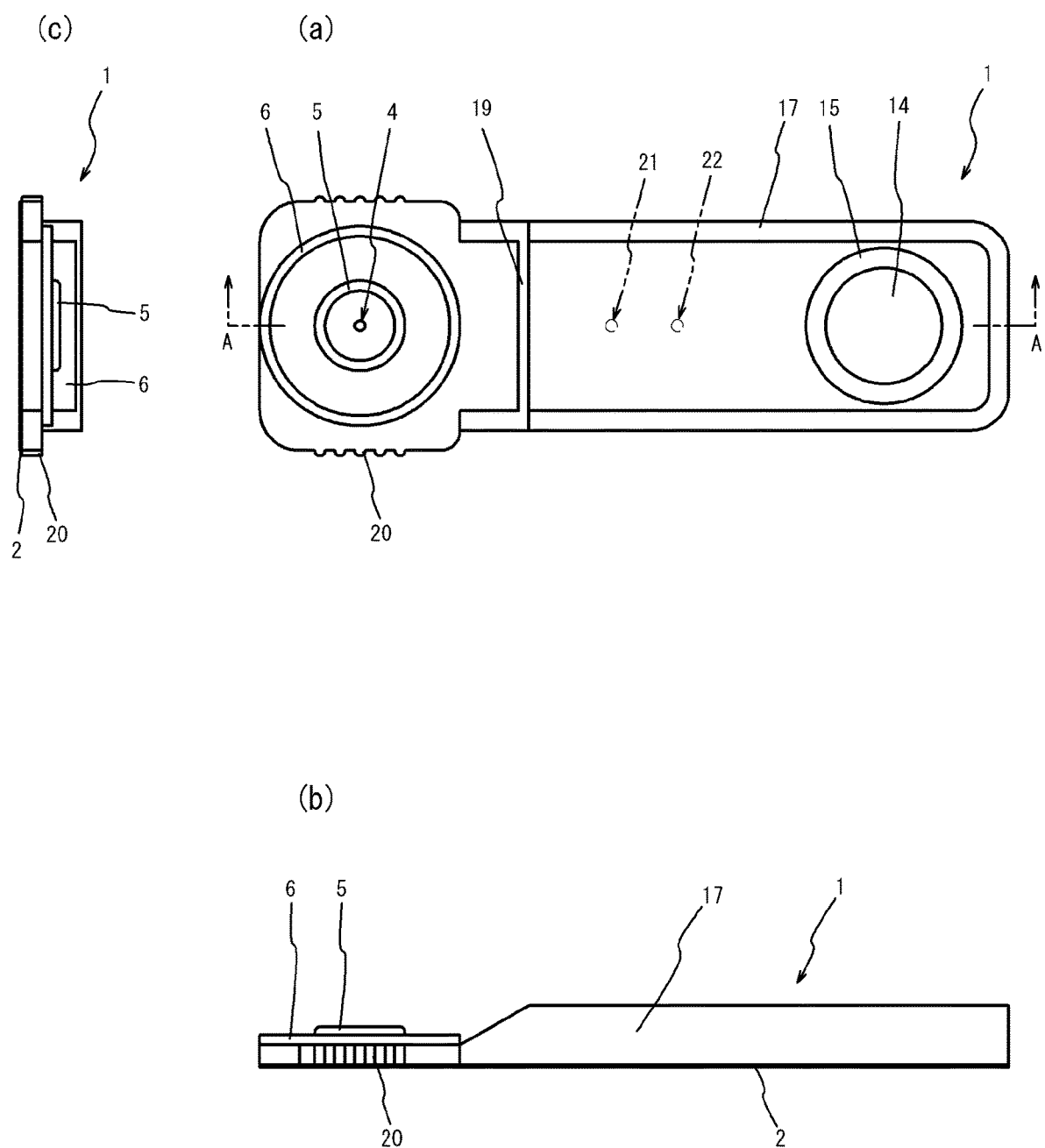
FIG. 2 is a view illustrating a blood clotting time measurement cartridge of a first embodiment, FIG. 2(a) being a plan view, FIG. 2(b) being a front view, and FIG. 2 (c) being a right side view.

In the following, a first embodiment of a blood clotting time measurement cartridge (hereinafter, referred to as cartridge) according to the present invention will be described with reference to FIG. 1 to FIG. 3.

The cartridge of the present embodiment includes a base 1 that is flat as a whole, and a sheet-like blocking plate 2 fixed to the base 1 on a bottom surface side of the base 1.

The base 1 is formed of a colorless transparent synthetic resin. Note that there is no limitation to synthetic resin, and glass or the like may be used. Also, there is no limitation to colorless transparency, and at least a detection area (described later) may have colored transparency with which light is transmitted. Also, what is other than the detection area does not need to be transparent. Also, although being formed of a colorless transparent synthetic resin (thin sheet) similarly to the base 1, the blocking plate 2 can be formed of various materials in various colors as long as a function of the present invention is satisfied. Also, connection between the base 1 and the blocking plate 2 may be adhered by something adhesive, or may be welded, for example, with an ultrasonic wave.

Figure 3:
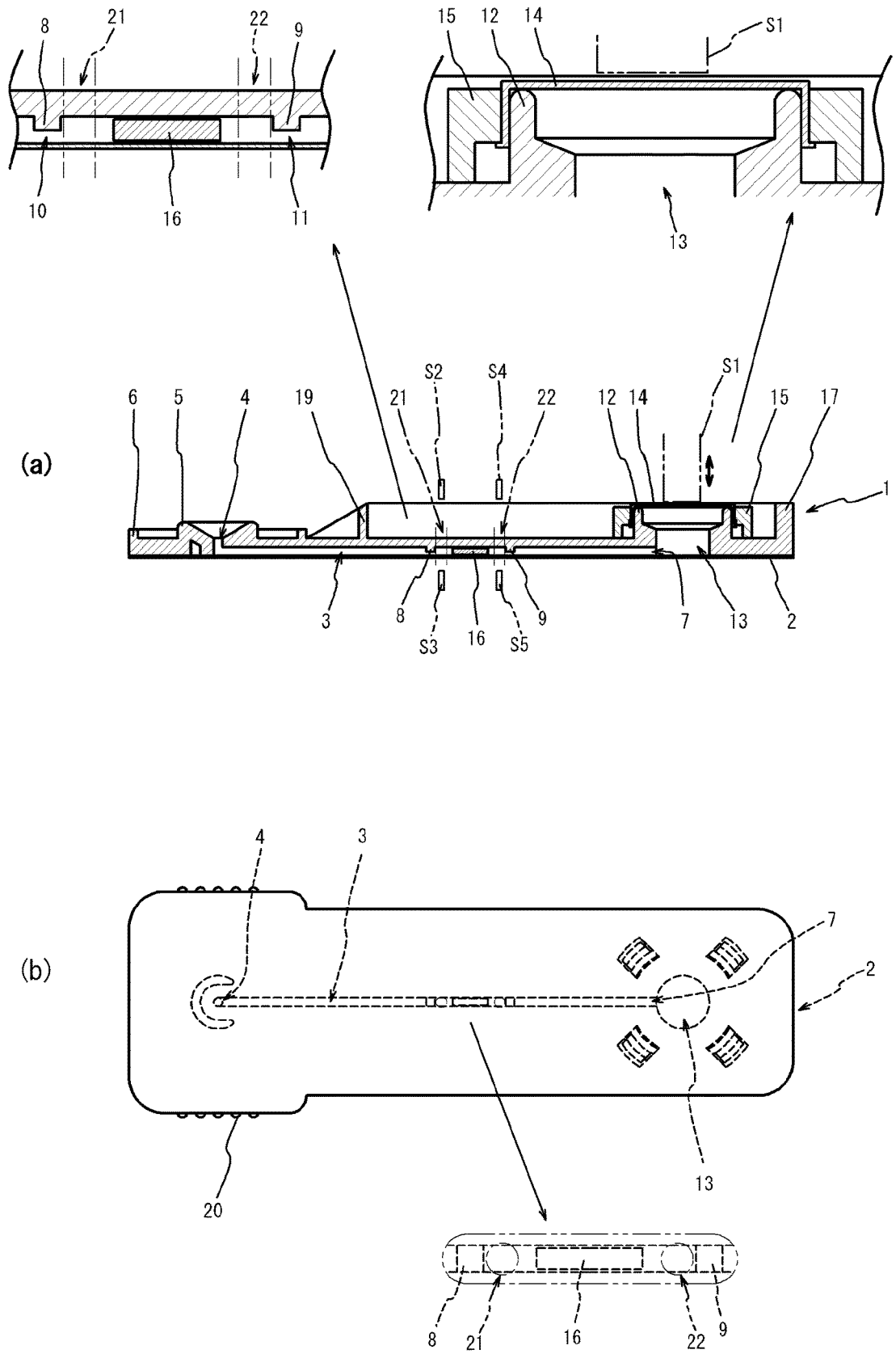
FIG. 3 is a view illustrating the blood clotting time measurement cartridge of the first embodiment, FIG. 3(a) being a sectional view along A-A indicated in FIG. 2(a), and FIG. 3(b) being a bottom view.

As illustrated in FIG. 3, a groove extended long with respect to a cross-sectional area is provided in a bottom surface of the base 1 and forms a measurement flow channel 3 with the blocking plate 2. One measurement flow channel 3 of the present embodiment is provided in a center part in a width direction of the base 1.

Then, an inlet 4 through which blood can be introduced is provided on one end side of the measurement flow channel 3. The inlet 4 is connected to an opening part 5 an outer peripheral surface of which has a columnar shape and an inner peripheral surface of which is provided in a conical shape. Also, a surplus blood receiving unit 6 having an annular shape is provided on an outer side in a radial direction of the opening part 5.

Also, a communication opening 7 is provided on the other end side of the measurement flow channel 3. Through the communication opening 7, it is possible to perform suction or pressure application with respect to air in the measurement flow channel 3 or blood introduced from the inlet 4 into the measurement flow channel 3 by changing a pushing amount into a diaphragm (described later).

Then, in a center part of the measurement flow channel 3, a one end-side protruded part 8 and an other end-side protruded part 9 provided in such a manner as to be protruded to a bottom surface side are provided. With this arrangement, as illustrated in an enlarged view in FIG. 3(a), narrowed parts (one end-side narrowed part 10 and other end-side narrowed part 11) where the measurement flow channel 3 is narrowed down are formed.

The base 1 includes a cylindrical wall 12 that has a cylindrical shape as a whole on an opposite side of the opening part 5 or the surplus blood receiving unit 6 described above. The inner peripheral surface of the cylindrical wall 12 has a shape in which a bottom surface side has a small diameter and a top surface side has a large diameter with a part having an increasing diameter therebetween. Then, an inner space of the cylindrical wall 12 is connected to the communication opening 7 on the bottom surface side. Note that a whole inner space of the cylindrical wall 12 will be referred to as an air chamber 13 in the present embodiment.

A diaphragm 14 that closes the air chamber 13 is provided on the top surface side of the cylindrical wall 12. The diaphragm 14 is formed, for example, of thin elastic rubber. Also, on an outer side in a radial direction of the cylindrical wall 12, an annular holder 15 that is fit into and held by the cylindrical wall 12 by piercing though the cylindrical wall 12 and that sandwiches the diaphragm 14 with the cylindrical wall 12 is provided. Here, when the diaphragm 14 is pushed toward the bottom surface side, a volume of the air chamber 13 becomes small. Thus, it is possible to apply pressure to the air chamber 13. Also, when the diaphragm 14 is pushed toward the bottom surface side in an initial state, a volume of the air chamber 13 becomes large when pushing is released. Thus, it is possible to reduce pressure of the air chamber 13. Note that the pressure of the air chamber 13 may be reduced by pulling of the diaphragm 14 toward the top surface side.

Then, in the measurement flow channel 3, a moving body 16 is arranged between the one end-side narrowed part 10 and the other end-side narrowed part 11. An outer diameter of the moving body 16 is formed in such a manner as to be slightly smaller than an inner diameter of the measurement flow channel 3 and can move inside the measurement flow channel 3. Also, a minute gap though which blood can pass is formed between an outer peripheral surface of the moving body 16 and an inner peripheral surface of the measurement flow channel 3. Note that an outer diameter of the moving body 16 is formed in such a manner as to be larger than a gap in the one end-side narrowed part 10, and the other end-side narrowed part 11. Here, the moving body 16 of the present embodiment has a columnar shape and is formed of aluminum. Note that a shape of the moving body 16 may be a prismatic shape, or an elliptical shape in which a thickness of an end part becomes small compared to a center part in a longitudinal direction. Alternatively, a spherical shape may be included. Then, various materials such as different metal or synthetic resin can be applied as a material of the moving body 16.

Incidentally, a clotting accelerator to accelerate clotting of blood is applied on a flow channel wall surface that defines the measurement flow channel 3 (inner surface of groove provided in center part in width direction of base 1 in present embodiment). Note that a clotting accelerator may be thoroughly applied on the measurement flow channel 3 by application also on a top surface of the blocking plate 2 that faces the measurement flow channel 3, or may be applied on the moving body 16.

Also, an outer edge wall 17 that is placed in an outer edge part of the base 1 and that forms a U shape substantially in a planar view around the holder 15 is provided on a top surface of the base 1. Also, as illustrated in FIG. 1, a plate-like part (shielding part) 19 that connects light and left outer edge walls 17 is provided between the surplus blood receiving unit 6 and the holder 15. Moreover, a finger holder part 20 that is a part which has an indented shape and in which a finger is placed in setting or detaching of a cartridge with respect to a blood clotting time measuring device (hereinafter, referred to as "measuring device") is provided in a vicinity of the surplus blood receiving unit 6 in a longitudinal side surface of the base 1.

Also, the base 1 and the blocking plate 2 have a detection area through which light can be transmitted with respect to a predetermined part in the measurement flow channel 3. In the present embodiment, as illustrated in FIG. 3(a), a one end-side detection area 21 placed on a side of the other end-side narrowed part 11 in a vicinity of the one end-side narrowed part 10, and an other end-side detection area 22 placed on a side of the one end-side narrowed part 10 in a vicinity of the other end-side narrowed part 11 are included. Note that the one end-side detection area 21 is placed on a side of the other end-side detection area 22 with respect to the shielding part 19.

Such a cartridge of the first embodiment can be set in a measuring device (not illustrated) and can measure clotting time of blood. More specifically, a side on which the diaphragm 14 is placed of the cartridge extended long is inserted into the measuring device, whereby the cartridge is set in the measuring device. Note that the opening part 5 is placed on an outer side of the measuring device in this state. Also, as illustrated in FIG. 3(a), the measuring device includes a pressing means S1 that can push the diaphragm 14 for a predetermined moving amount, and a detection means that can detect existence/non-existence of the moving body 16 with light. The detection means in the present embodiment includes a one end-side light source S2 and a one end-side light receiving sensor S3 that are provided in such a manner as to sandwich the measurement flow channel 3 in the one end-side detection area 21, and an other end-side light source S4 and an other end side light receiving sensor S5 in the other end-side detection area 22. Since the moving body 16 blocks light from the one end-side light source S2 or the other end-side light source S4, it is possible to detect whether the moving body 16 is in the one end-side detection area 21 or the other end-side detection area 22. Note that the one end-side light source S2 and the other end-side light source S4 emit an infrared ray. Also, positions of the one end-side light source S2, the one end-side light receiving sensor S3, the other end-side light source S4, and the other end side light receiving sensor S5 may be reversed from the illustrated example, and the one end-side light source S2 and the other end-side light source S4 may be provided on a bottom surface side of the cartridge, and the one end-side light receiving sensor S3 and the other end side light receiving sensor S5 may be provided on a top surface side of the cartridge. Also, a reflection-type sensor may be used instead of such a transmission-type sensor.

Then, after the cartridge is set in the measuring device, blood to be measured is injected into an inner side of the opening part 5 by a dispensing burette or the like. Note that it is assumed that the diaphragm 14 is pushed previously by the pressing means S1 and a volume of the air chamber 13 is reduced in injection of the blood. Here, an adequate injection amount of the blood is in a degree of not causing spilling from the opening part 5. However, even in a case where the blood is injected more, it is possible to store the blood spilt from the opening part 5 into the surplus blood receiving unit 6 since the surplus blood receiving unit 6 is provided on the outer side in the radial direction of the opening part 5. Moreover, since the shielding part 19 is provided on an outer side of the surplus blood receiving unit 6, the blood does not flow into the one end-side detection area 21 or the other end-side detection area 22 even when overflowing from the surplus blood receiving unit 6.

Subsequently, the pressure of the air chamber 13 is reduced when the pushed pressing means S1 is pulled back. Thus, it is possible to suction the air in the measurement flow channel 3 from the communication opening 7, and to suction the blood injected to the opening part 5 into the measurement flow channel 3. Note that it is assumed that the blood is suctioned beyond the other end-side narrowed part 11 in this state. With this arrangement, the moving body 16 moves along with the blood to a side of the other end-side narrowed part 11. Here, it is possible to check whether the moving body 16 moves to the vicinity of the other end-side narrowed part 11 by checking whether light from the other end-side light source S4 can be detected by the other end side light receiving sensor S5.

Subsequently, the pressing means S1 is pushed again and pressure is applied to the air chamber 13. Since the pressure is also applied to the air or the blood in the measurement flow channel 3 in association with this, the moving body 16 moves toward the one end-side narrowed part 10 along with the blood. Here, as described above, by the one end-side light source S2 and the one end-side light receiving sensor S3, it is detected whether the moving body 16 moves to the vicinity of the one end-side narrowed part 10.

Since it is possible to apply pressure or to reduce pressure with respect to the air chamber 13 by repeating pushing and pulling of the pressing means S1 in such a manner, pressure application or suction of the air or the blood in the measurement flow channel 3 is performed through the communication opening 7. In association with this, it is possible to make the moving body 16 make a reciprocating motion along with the blood. With this arrangement, the blood in the measurement flow channel 3 is stirred by the moving body 16, whereby it is possible to efficiently and stably dissolve the clotting accelerator applied on the flow channel wall surface that defines the measurement flow channel 3. Note that the moving body 16 does not move beyond the one end-side narrowed part 10 and the other end-side narrowed part 11 during the reciprocating motion since the outer diameter thereof is formed in such a manner as to be larger than the gap in the one end-side narrowed part 10, and the other end-side narrowed part 11. Also, when the air is taken into the blood injected into the cartridge, there is a case where an air bubble is generated in the measurement flow channel 3, and a case where this air bubble is erroneously detected as clotted blood in a conventional cartridge. However, in the present embodiment, since the moving body 16 is detected while a threshold of the one end-side light receiving sensor S3 or the like is optimized, it is possible to control an influence of the air bubble on blood clotting time measurement.

Then, when a clotting accelerator is dissolved by stirring of the blood by the moving body 16, the blood is gradually clotted and movement of the moving body 16 becomes slow gradually. That is, since a cycle of a reciprocating motion of the moving body 16 detected by the one end-side light receiving sensor S3 and the other end side light receiving sensor S5 in a state in which the blood is not clotted, and a cycle of a reciprocating motion detected by the one end-side light receiving sensor S3 or the like when movement of the moving body 16 becomes slow are different even when timing of pushing or pulling the pressing means S1 is not changed, it is possible to calculate clotting time of the blood on the basis of this variation in time necessary for a reciprocating motion. As described above, a minute gap through which the blood can pass is formed between the outer peripheral surface of the moving body 16 and the inner peripheral surface of the measurement flow channel 3, and movement of the moving body 16 becomes slow when clotting of the blood is started in this gap. That is, a cycle of a reciprocating motion of the moving body 16 becomes longer than that preceding clotting of the blood. Thus, it is possible to obtain clotting time of the blood from this difference in a cycle. Note that since this gap is small, movement of the moving body 16 is influenced immediately when the blood starts to be clotted. Thus, it is possible to measure clotting time of the blood in a short period.

Figure 4:
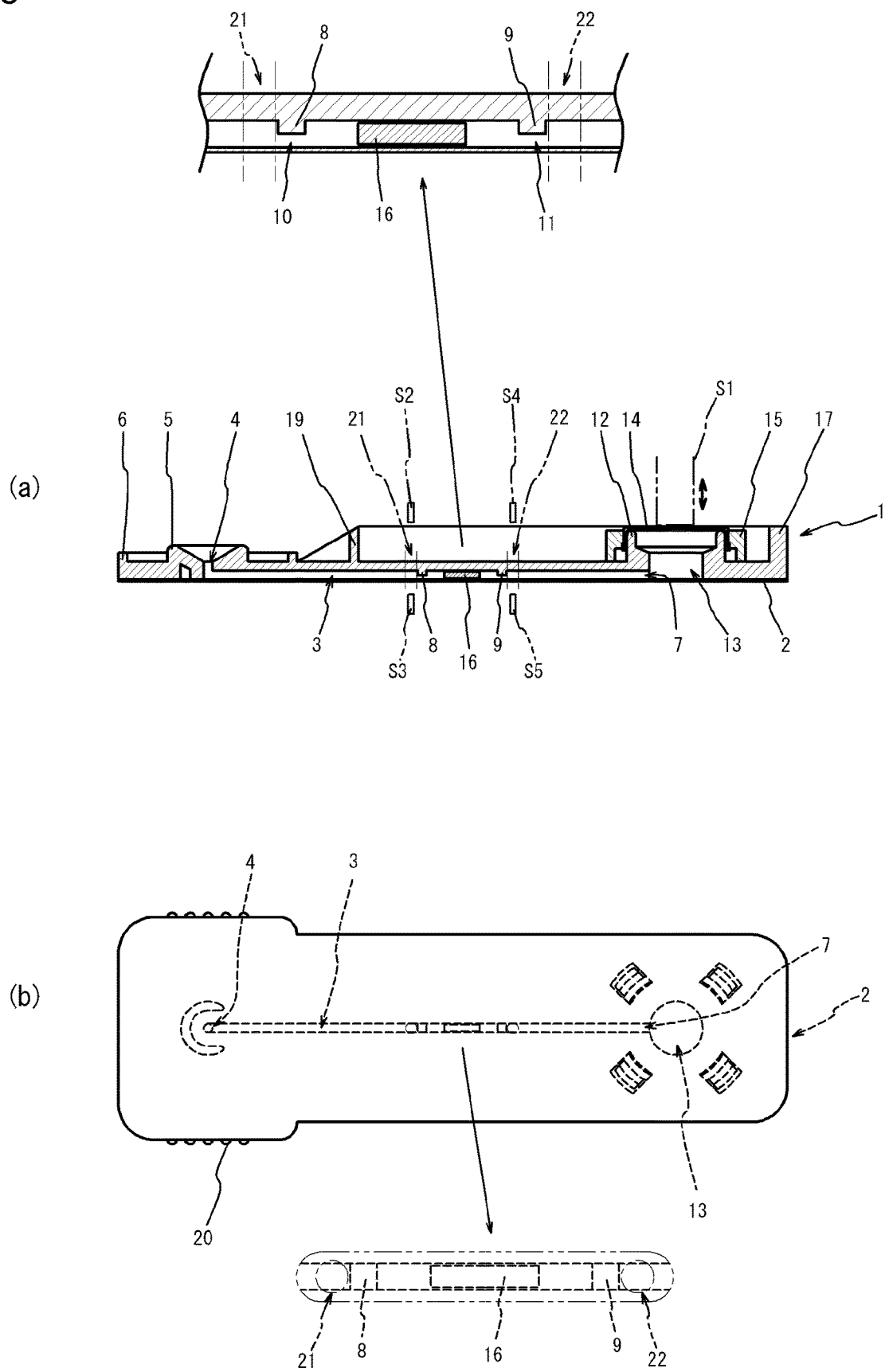
FIG. 4 is a view illustrating a modification example of the first embodiment.

The moving body 16 that makes a reciprocating motion is detected by the one end-side light receiving sensor S3 or the like in the present embodiment. However, an object of detection by the one end-side light receiving sensor S3 may be the blood. In this case, a mass of the blood becomes large when clotting is advanced, and blocks the one end-side narrowed part 10 or the other end-side narrowed part 11. Thus, a flow of the blood that makes a reciprocating motion is interrupted and the blood detected by the one end-side light receiving sensor S3 or the other end-side light source S4 before this is brought into an undetectable state. Thus, it is possible to measure clotting time of the blood on the basis of time at which detection of the blood by the one end-side light receiving sensor S3 or the other end-side light source S4 becomes impossible. Note that in a case where the blood is detected by the one end-side light receiving sensor S3 or the like, the one end-side detection area 21 may be placed on an opposite side of the other end-side narrowed part 11 in the vicinity of the one end-side narrowed part 10, and the other end-side detection area 22 may be placed on an opposite side of the one end-side narrowed part 10 in the vicinity of the other end-side narrowed part 11, as illustrated in FIG. 4.

Figure 5:
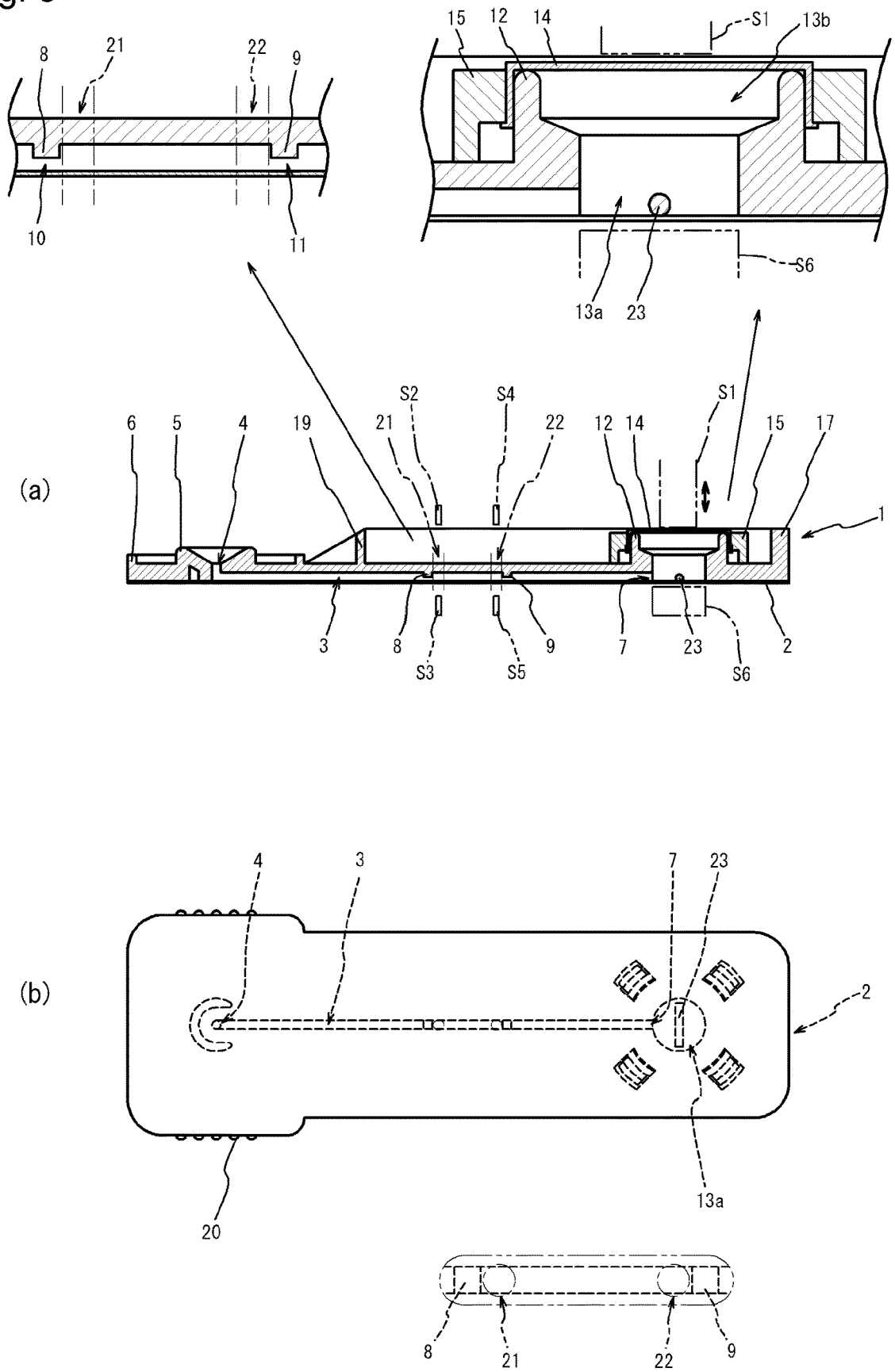
FIG. 5 is a view illustrating a second embodiment of a blood clotting time measurement cartridge according to the present invention, FIG. 5(a) being a sectional view corresponding to A-A indicated in FIG. 2(a), and FIG. 5(b) being a bottom view.

Next, a second embodiment of a cartridge according to the present invention will be described. As illustrated in FIG. 5, the cartridge of the present embodiment includes a stirring bar 23 instead of the moving body 16 in the above-described cartridge of the first embodiment. Also, in the present embodiment, a space on a bottom surface side which space is connected to a communication opening 7 (basically, space that have small diameter and that is placed on bottom surface side in inner space of cylindrical wall 12) will be referred to as a storage chamber 13a, and a space on a top surface side which space is closed by a diaphragm 14 (basically, space having increasing diameter and space that have large diameter and that is connected thereto in inner space of cylindrical wall 12) will be referred to as an air chamber 13b in an inner space of a cylindrical wall 12. Note that since the other parts are basically identical to those of the cartridge in the first embodiment, the same sign is assigned in the drawing and a description thereof is omitted.

The stirring bar 23 is arranged in the storage chamber 13a. The stirring bar 23 is formed, for example, of a magnet or a ferromagnetic body, and is rotated in the storage chamber 13a by a magnetic field generating unit S6 provided in a measuring device. Also, although having a columnar shape, the stirring bar 23 of the present embodiment may have a prismatic shape, or an elliptical shape in which a thickness of an end part becomes small compared to a center part in a longitudinal direction. Also, a plurality of wings may be provided in a disk-shaped part.

Also, a clotting accelerator to accelerate clotting of blood is applied on a storage chamber wall surface that defines the storage chamber 13a (inner peripheral surface that have small diameter and that is placed on bottom surface side in inner peripheral surface of cylindrical wall 12 in present embodiment). Note that similarly to the cartridge of the first embodiment, the clotting accelerator may be applied on a flow channel wall surface that defines a measurement flow channel 3 or may be applied on the stirring bar 23.

Such a cartridge of the second embodiment can be also set in a measuring device (not illustrated) and measure clotting time of blood.

More specifically, similarly to the cartridge of the first embodiment, the diaphragm 14 is previously pushed by a pressing means S1, and blood is injected into an inner side of an opening part 5 with a dispensing burette or the like.

Then, pressure of the air chamber 13b is reduced by pulling back of the pushed pressing means S1. Thus, it is possible to suction the air in the measurement flow channel 3 from the communication opening 7 through the storage chamber 13a, and to suction the blood injected to the opening part 5 into the measurement flow channel 3. Here, the blood is suctioned beyond the other end-side narrowed part 11 and up to the storage chamber 13a in the present embodiment. Note that since there is a correlation between a pulled amount of the pressing means S1 and an amount of suctioned blood, it is possible to determine whether the blood is suctioned up to the storage chamber 13a on the basis of the pulled amount of the pressing means S1. Incidentally, in a one end-side light receiving sensor S3 and an other end side light receiving sensor S5 in the present embodiment, a threshold is optimized in such a manner that existence/non-existence of the blood is detected. Thus, it is possible to detect whether the blood is moved to a vicinity of a one end-side narrowed part 10 on the basis of whether light from a one end-side light source S2 can be detected by a one end-side light receiving sensor S3. Also, it is possible to detect whether the blood is moved to a vicinity of an other end-side narrowed part 11 on the basis of whether light from an other end-side light source S4 can be detected by an other end side light receiving sensor S5. Thus, with a time point at which the blood is detected by the one end-side light receiving sensor S3 or the other end side light receiving sensor S5 as a reference of a pulled amount of the pressing means S1, the blood may be suctioned up to the storage chamber 13a on the basis of a pulled amount therefrom.

After the blood is suctioned up to the storage chamber 13a, the stirring bar 23 is rotated by driving of the magnetic field generating unit S6. With this arrangement, a clotting accelerator applied on the storage chamber wall surface that defines the storage chamber 13a can be efficiently and stably dissolved in the blood.

Then, when the pressing means S1 is pushed again while the stirring bar 23 is kept rotated (rotation may be stopped), pressure is applied to the air chamber 13b. Accordingly, since pressure is also applied to the blood in the storage chamber 13a and the measurement flow channel 3, it is possible to make the blood flow toward the one end-side narrowed part 10. By repetition of pushing and pulling of the pressing means S1 in such a manner, it is possible to make the blood make a reciprocating motion in the measurement flow channel 3.

The blood is gradually clotted when the clotting accelerator is dissolved by stirring of the blood by the stirring bar 23, whereby a mass of the blood becomes large and blocks the one end-side narrowed part 10 or the other end-side narrowed part 11. Accordingly, a flow of the blood making a reciprocating motion is interrupted, and the blood that is detected by the one end-side light receiving sensor S3 or the other end-side light source S4 before this is brought into an undetectable state. Thus, it is possible to measure clotting time of the blood on the basis of time at which detection of the blood by the one end-side light receiving sensor S3 or the other end-side light source S4 becomes impossible.

Figure 6:
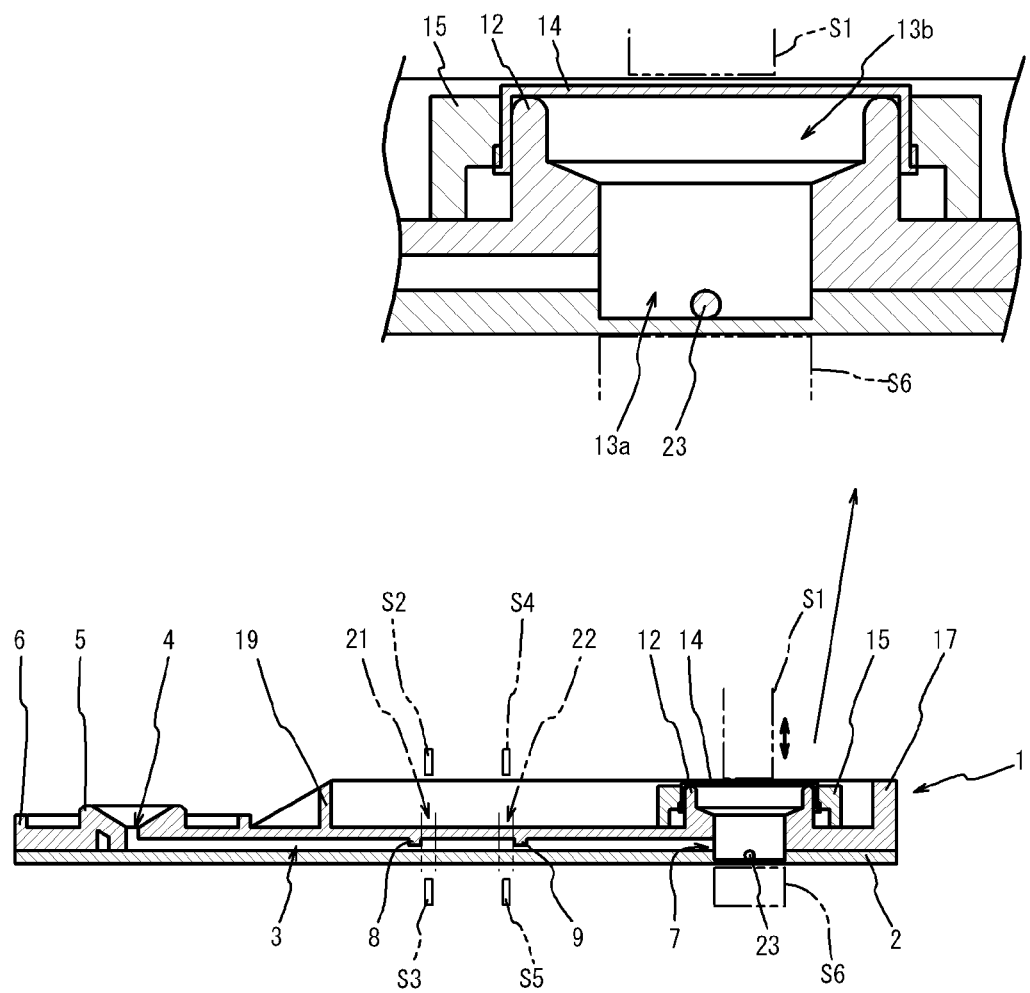
FIG. 6 is a view illustrating a modification example of the second embodiment.

In the above-described cartridge, the storage chamber 13a and the measurement flow channel 3 illustrated in FIG. 5 are in the same position on the bottom surface side. However, as illustrated in FIG. 6, a step may be provided in such a manner that a storage chamber 13a is placed on a bottom surface side of a measurement flow channel 3. Since the stirring bar 23 pulled by the magnetic field generating unit S6, the stirring bar 23 does not move to an outer side of the storage chamber 13a (measurement flow channel 3) even in the cartridge illustrated in FIG. 5. However, when the step is provided in a manner of the cartridge illustrated in FIG. 6, it is possible to more securely keep a stirring bar 23 in a storage chamber 13a. Also, various methods can be employed as a method of fixing the diaphragm 14. For example, fixation to a base 1 may be performed by utilization of an adhesive or the like. Also, a detection area may be provided in only one of the one end side and the other end side.

Next, a third embodiment of a cartridge according to the present invention will be described. The cartridge of the present embodiment includes a base 101 that is flat as a whole, and a sheet-like blocking plate 102 fixed to the base 101 on a bottom surface side of the base 101.

The base 101 is formed of a colorless transparent synthetic resin. Note that there is no limitation to synthetic resin, and glass or the like may be used. Also, there is no limitation to colorless transparency, and at least a detection area (described later) may have colored transparency with which light is transmitted. Also, what is other than the detection area does not need to be transparent. Also, although being formed of a colorless transparent synthetic resin (thin sheet) similarly to the base 101, the blocking plate 102 can be formed of various materials in various colors as long as a function of the present invention is satisfied. Also, connection between the base 101 and the blocking plate 102 may be adhered by something adhesive, or may be welded, for example, with an ultrasonic wave.

Figure 9:
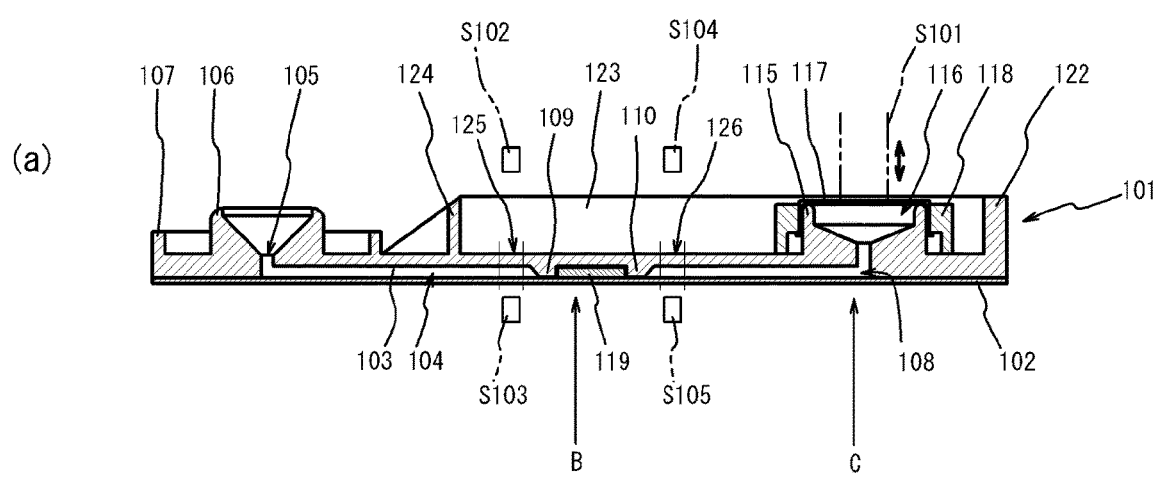
FIG. 9 is a view related to the blood clotting time measurement cartridge illustrated in FIG. 7, FIG. 9(a) being a sectional view along A-A indicated in FIG. 8(a), and FIG. 9(b) being a bottom view.
Figure 9:
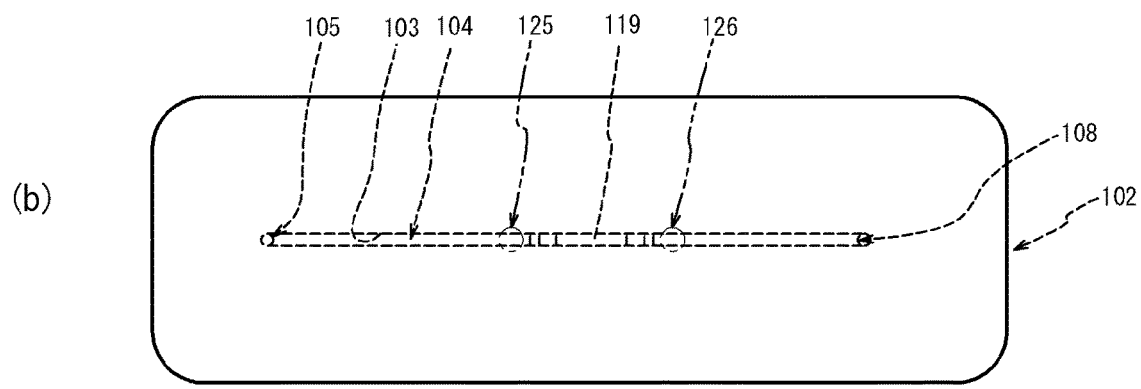

As illustrated in FIG. 9, a groove part 103 extended long with respect to a cross-sectional area is provided in a bottom surface of the base 101, and a measurement flow channel 104 that houses blood in a manner described later is formed between the groove part 103 and the blocking plate 102.

Then, an inlet 105 through which blood can be introduced is provided on one end side of the measurement flow channel 104. The inlet 105 is connected to an opening part 106 an outer peripheral surface of which has a columnar shape and an inner peripheral surface of which is provided in a conical shape. Also, a surplus blood receiving unit 107 having an annular shape is provided on an outer side in a radial direction of the opening part 106.

Also, a communication opening 108 is provided on the other end side of the measurement flow channel 104. The communication opening 108 can suction or apply pressure with respect to air in the measurement flow channel 104 or blood introduced from the inlet 105 into the measurement flow channel 104 by changing a pushing amount into a diaphragm (described later).

Figure 10:
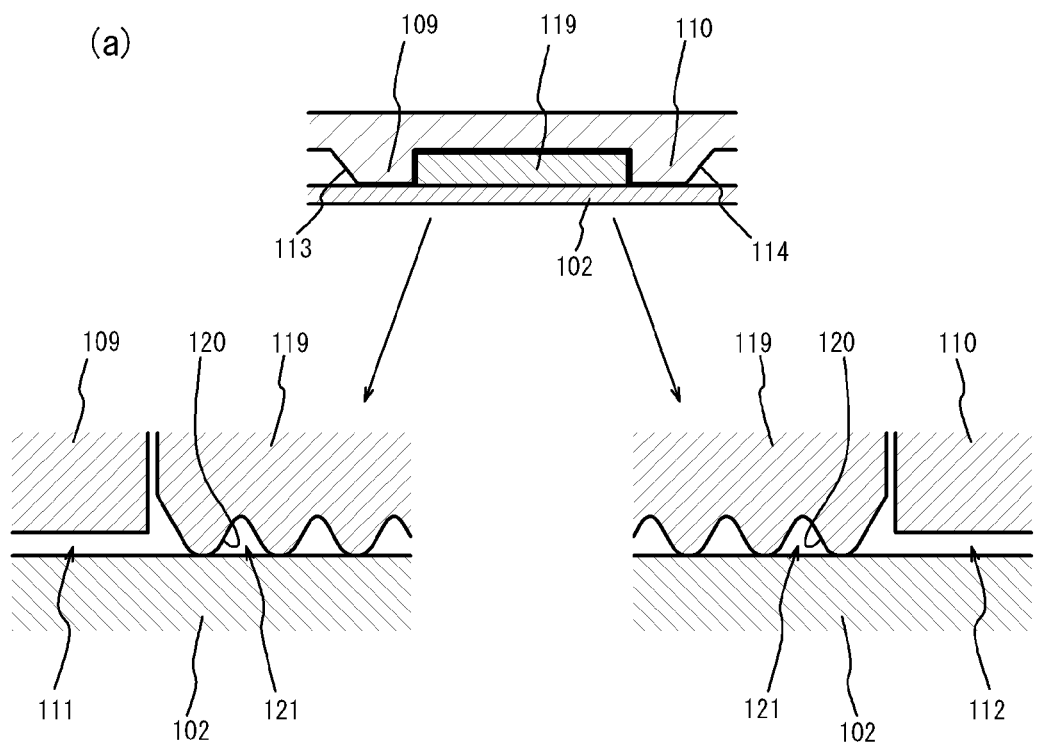
FIG. 10(a) is a partially-enlarged sectional view of a B part in FIG. 9.
FIG. 10(b) is a partially-enlarged view of a C part in FIG. 9.
Figure 10:
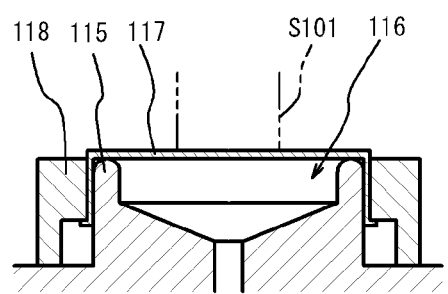

Then, a pair of protruded parts (one end-side protruded part 109 and other end-side protruded part 110) provided in such a manner as to be protruded to a bottom surface side is provided in a center part of the measurement flow channel 104. With this arrangement, a narrowed part (one end-side narrowed part 111 and other end-side narrowed part 112) in which the measurement flow channel 104 is narrowed down is formed as illustrated in an enlarged view in FIG. 10(a). Also, in the one end-side protruded part 109, an inclination surface (one end-side inclination surface 113) is provided on an opposite side of a side where the other end-side protruded part 110 is placed. Similarly, in the other end-side protruded part 110, an inclination surface (other end-side inclination surface 114) is provided on an opposite side of a side where the one end-side protruded part 109 is placed.

The base 101 includes a cylindrical wall 115 that has a cylindrical shape as a whole on an opposite side of the opening part 106 or the surplus blood receiving unit 107 described above (see FIG. 9(a)). The inner peripheral surface of the cylindrical wall 115 has a shape in which a bottom surface side has a small diameter and a top surface side has a large diameter with a part having an increasing diameter therebetween. Then, an inner space of the cylindrical wall 115 is connected to the communication opening 108 on the bottom surface side. Note that a whole inner space of the cylindrical wall 115 will be referred to as an air chamber 116 in the present embodiment.

A diaphragm 117 that closes the air chamber 116 is provided on the top surface side of the cylindrical wall 115. The diaphragm 117 is formed, for example, of thin elastic rubber. Also, on an outer side in a radial direction of the cylindrical wall 115, an annular holder 118 that is fit into and held by the cylindrical wall 115 by piercing though the cylindrical wall 115 and that sandwiches the diaphragm 117 with the cylindrical wall 115 is provided. Here, when the diaphragm 117 is pushed toward the bottom surface side, a volume of the air chamber 116 becomes small. Thus, it is possible to apply pressure to the air chamber 116. Also, when the diaphragm 117 is pushed toward the bottom surface side in an initial state, a volume of the air chamber 116 becomes large when pushing is released. Thus, it is possible to reduce pressure of the air chamber 116. Note that the pressure of the air chamber 116 may be reduced by pulling of the diaphragm 117 toward the top surface side.

Then, on an inner side of the groove part 103, a shaft-like member 119 is housed between the one end-side protruded part 109 and the other end-side protruded part 110. An outer diameter of the shaft-like member 119 is substantially the same as or a slightly smaller than an inner diameter of the measurement flow channel 104, and an entire length of the shaft-like member 119 is substantially the same as or slightly shorter than a distance between the one end-side protruded part 109 and the other end-side protruded part 110. Thus, the shaft-like member 119 is hardly moved in the groove part 103. Then, as illustrated in a partially-enlarged view in FIG. 10(a), a helical groove part 120 winding in a helical manner is provided in the surface of the shaft-like member 119. With this arrangement, a helical flow channel 121 is formed between wall surfaces of the groove part 103 and the blocking plate 102 and an outer peripheral surface of the shaft-like member 119. Here, the shaft-like member 119 of the present embodiment is formed by utilization of a male screw (such as male screw of Ml). Thus, the shaft-like member 119 can be formed inexpensively.

Incidentally, in the measurement flow channel 104 including the helical flow channel 121, a clotting accelerator to accelerate clotting of blood is applied on the wall surface of the groove part 103 that defines these flow channels. Note that the clotting accelerator may be applied on the wall surface of the blocking plate 102 that faces the measurement flow channel 104, or the outer peripheral surface of the shaft-like member 119.

Figure 7:
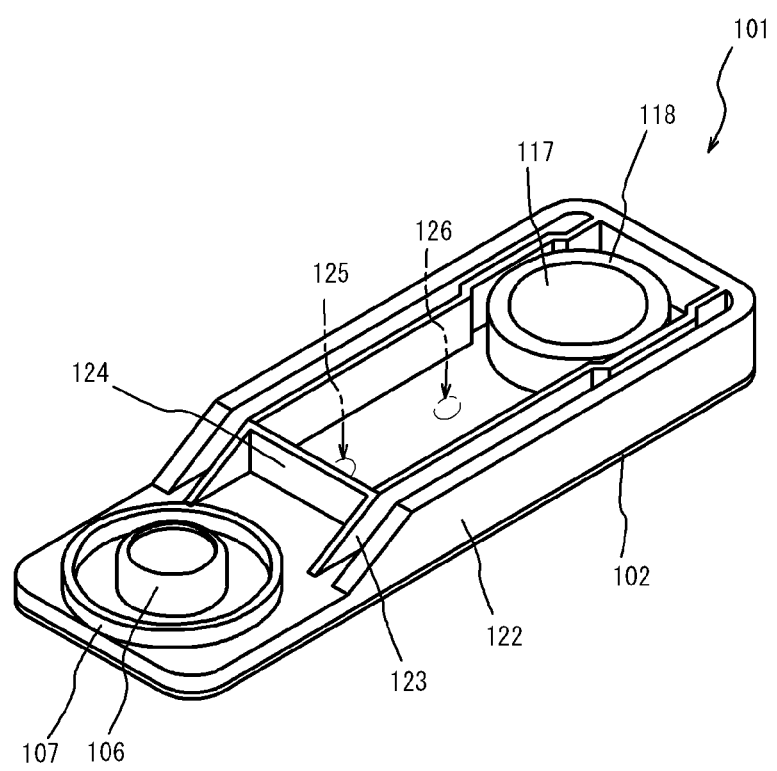
FIG. 7 is a perspective view illustrating a third embodiment of a blood clotting time measurement cartridge according to the present invention.
Figure 8:
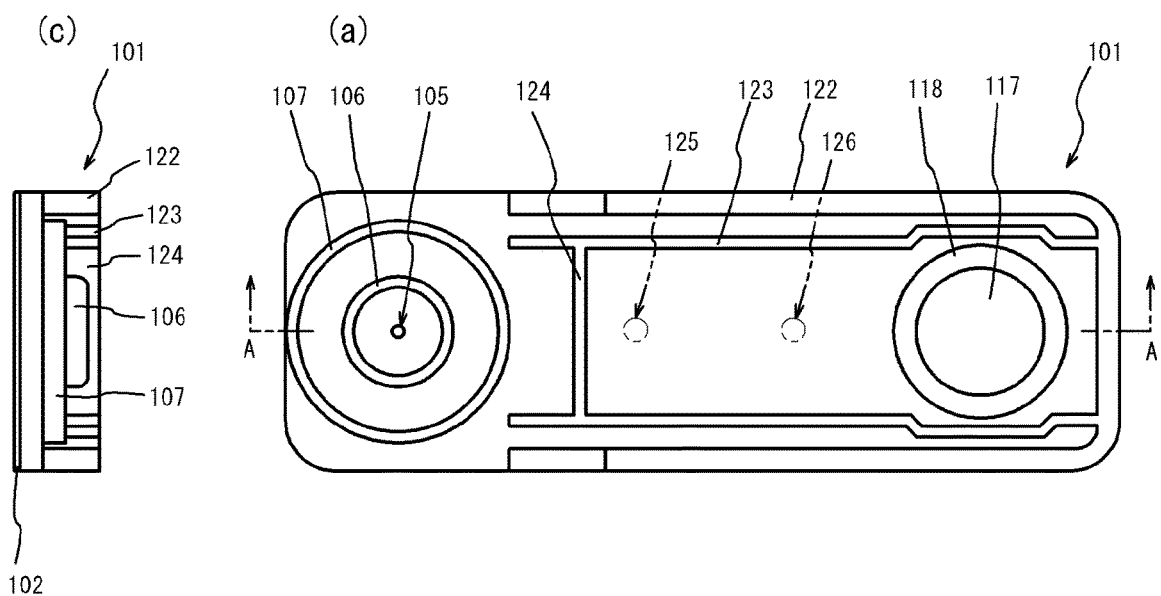
FIG. 8 is a view related to the blood clotting time measurement cartridge illustrated in FIG. 7, FIG. 8 (a) being a plan view, FIG. 8(b) being a front view, and FIG. 8(c) being a right side view.
Figure 8:
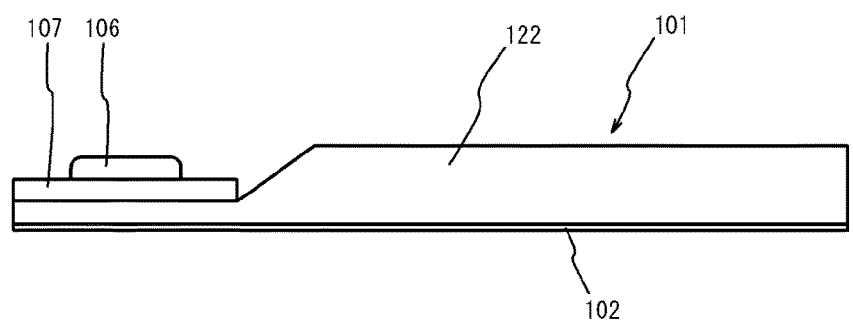

Also, as illustrated in FIG. 7 and FIG. 8, an outer edge wall 122 that is placed in an outer edge part of the base 101 and that forms a U shape substantially in a planar view around the holder 118 is provided on a top surface of the base 101. Also, a pair of inner side walls 123 is provided on an inner side in a width direction of the outer edge wall 122. Moreover, a plate-like part (shielding part) 124 that connects the pair of inner side walls 123 is provided between the surplus blood receiving unit 107 and the holder 118.

Also, the base 101 and the blocking plate 102 have a detection area through which light can be transmitted with respect to a predetermined part in the measurement flow channel 104. In the present embodiment, as illustrated in FIG. 9(a), a one end-side detection area 125 that is placed on a side of the inlet 105 in a vicinity of the one end-side protruded part 109, and an other end-side detection area 126 that is placed on a side of the communication opening 108 in a vicinity of the other end-side protruded part 110 are included. Note that the one end-side detection area 125 is placed on a side of the other end-side detection area 126 with respect to a shielding part 124.

The cartridge of the present embodiment in such a configuration can be set in a blood clotting time measuring device (hereinafter, referred to as "measuring device") (not illustrated) and can measure clotting time of blood. More specifically, a side on which the diaphragm 117 is placed of the cartridge extended long is inserted into the measuring device, whereby the cartridge is set in the measuring device. Note that the opening part 106 is placed on an outer side of the measuring device in this state. Also, as illustrated in FIG. 9(a), a pressing means S101 that can push the diaphragm 117 for a predetermined moving amount, and a detection means that can detect existence/non-existence of blood with light are provided in the measuring device. In the detection means in the present embodiment, a one end-side light source S102 and a one end-side light receiving sensor S103 provided in such a manner as to sandwich the measurement flow channel 104 are included in the one end-side detection area 125, and an other end-side light source S104 and an other end side light receiving sensor S105 are included in the other end-side detection area 126. Here, the one end-side light source S102 and the other end-side light source S104 emit an infrared ray, and the one end-side light receiving sensor S103 and the other end side light receiving sensor S105 receive the emitted infrared ray. Here, in the one end-side light receiving sensor S103 and the other end side light receiving sensor S105 of the present embodiment, a threshold is optimized in such a manner that existence/non-existence of blood can be detected depending on a transmission degree of the emitted infrared ray. Note that positions of the one end-side light source S102, the one end-side light receiving sensor S103, the other end-side light source S104, and the other end side light receiving sensor S105 may be reversed from the illustrated example, and the one end-side light source S102 and the other end-side light source S104 may be provided on a bottom surface side of the cartridge, and the one end-side light receiving sensor S103 and the other end side light receiving sensor S105 may be provided on a top surface side of the cartridge. Also, a reflection-type sensor may be used instead of such a transmission-type sensor.

Then, after the cartridge is set in the measuring device, blood to be measured is injected into an inner side of the opening part 106 by a dispensing burette or the like. Note that it is assumed that the diaphragm 117 is pushed previously by the pressing means S101 and a volume of the air chamber 116 is reduced in injection of the blood. Here, an adequate injection amount of the blood is in a degree of not causing spilling from the opening part 106. However, even in a case where the blood is injected more, it is possible to store the blood spilt from the opening part 106 into the surplus blood receiving unit 107 since the surplus blood receiving unit 107 is provided on the outer side in the radial direction of the opening part 106. Moreover, since the shielding part 124 is provided on an outer side of the surplus blood receiving unit 107, the blood does not flow into the one end-side detection area 125 or the other end-side detection area 126 even when overflowing from the surplus blood receiving unit 107.

Subsequently, the pressure of the air chamber 116 is reduced when the pushed pressing means S101 is pulled back. Thus, it is possible to suction the air in the measurement flow channel 104 from the communication opening 108, and to suction the blood injected to the opening part 106 into the measurement flow channel 104. Note that the blood is suctioned beyond the other end-side narrowed part 112 while passing through the helical flow channel 121 in this state. It is possible to determine whether the blood is suctioned beyond the other end-side narrowed part 112 on the basis of whether the blood is detected by the other end side light receiving sensor S105. Note that since there is a correlation between a pulled amount of the pressing means S101 and a suctioned amount of the blood, determination may be made on the basis of the pulled amount of the pressing means S101. Also, with a time point at which the blood is detected by the one end-side light receiving sensor S103 as a reference of the pulled amount of the pressing means S101, the blood may be suctioned beyond the other end-side narrowed part 112 on the basis of a pulled amount therefrom.

Subsequently, the pressing means S101 is pushed again and pressure is applied to the air chamber 116, and the blood in the measurement flow channel 104 is moved toward the one end-side narrowed part 111. Accordingly, it is possible to oppositely move the blood passing through the helical flow channel 121 toward the other end-side narrowed part 112.

Since it is possible to apply pressure or to reduce pressure with respect to the air chamber 116 by repeating pushing and pulling of the pressing means S101 in such a manner, the air or the blood in the measurement flow channel 104 receives pressure or is suctioned through the communication opening 108, and it is possible to make the blood make a reciprocating motion in association therewith. That is, since a direction of a flow is switched, the blood can be stirred. Also, since a speed of a flow varies when the blood passes through the one end-side narrowed part 111 or the other end-side narrowed part 112, stirring is also performed efficiently in this point. Moreover, since the blood is made to pass through the helical flow channel 121, stirring thereof can be performed more efficiently. By the stirring of the blood in such a manner, it is possible to efficiently and stably dissolve the clotting accelerator applied on the wall surface of the groove part 103, or the like into blood.

Then, when the blood is stirred and the clotting accelerator is dissolved, viscosity of the blood is increased, and a flow of the blood becomes deteriorated in the one end-side narrowed part 111, the other end-side narrowed part 112, the helical flow channel 121, or the like. That is, since a cycle of a reciprocating motion of the blood detected by the one end-side light receiving sensor S103 and the other end side light receiving sensor S105 in a state in which the blood is not clotted, and a cycle of a reciprocating motion detected by the one end-side light receiving sensor S103 or the like when a flow of the blood is deteriorated are different even when timing of pushing or pulling the pressing means S101 is not changed, it is possible to calculate clotting time of the blood on the basis of this variation in time necessary for a reciprocating motion.

Note that when a speed of a flow or the like varies suddenly when the blood passes through the one end-side narrowed part 111 or the other end-side narrowed part 112, there is a case where air in the measurement flow channel 104 is involved and an air bubble is generated, and there is a possibility that this bubble influences detection of the blood in the one end-side light receiving sensor S103 and the other end side light receiving sensor S105. On the one hand, in the present embodiment, a speed of the like of a flow is made to vary gradually by provision of the one end-side inclination surface 113 and the other end-side inclination surface 114. Thus, the air bubble is less likely to be generated, and accuracy in detection of existence/non-existence of the blood can be more stabilized.

The helical flow channel 121 may be what includes a helical groove in a base 101 although including the groove part 103 provided in the base 101, and the shaft-like member 119 housed in this groove part 103 in the above-described cartridge of the third embodiment. Also, various methods can be employed as a method of fixing the diaphragm 117. For example, fixation to the base 101 may be performed by utilization of an adhesive or the like. Also, a detection area may be provided in any one of one end side and the other end side, or may be provided in three or more places. Moreover, as illustrated in FIG. 9, in the present embodiment, the one end-side detection area 125 is provided between the inlet 105 and the shaft-like member 119, and the other end-side detection area 126 is provided between the communication opening 108 and the shaft-like member 119. However, both detection areas may be provided between an inlet 105 and a shaft-like member 119, or may be provided between a communication opening 108 and a shaft-like member 119.

REFERENCE SIGNS LIST 1 base
2 blocking plate
3 measurement flow channel
4 inlet
5 opening part
6 surplus blood receiving unit
7 communication opening
8 one end-side protruded part
9 other end-side protruded part
10 one end-side narrowed part
11 other end-side narrowed part
12 cylindrical wall
13 air chamber
13a storage chamber
13b air chamber
14 diaphragm
15 holder
16 moving body
17 outer edge wall
19 shielding part
20 finger holder part
21 one end-side detection area
22 other end-side detection area
23 stirring bar
101 base
102 blocking plate
103 groove part
104 measurement flow channel
105 inlet
106 opening part
107 surplus blood receiving unit
108 communication opening
109 one end-side protruded part
110 other end-side protruded part
111 one end-side narrowed part
112 other end-side narrowed part
113 one end-side inclination surface
114 other end-side inclination surface
115 cylindrical wall
116 air chamber
117 diaphragm
118 holder
119 shaft-like member
120 helical groove part
121 helical flow channel
122 outer edge wall
123 inner side wall
124 shielding part
125 one end-side detection area
126 other end-side detection area

The invention claimed is:
1. A blood clotting time measurement cartridge comprising:
a base;
a measurement flow channel provided on a bottom side of the base and extended long with respect to a cross-sectional area;
an inlet which is provided on one end side of the measurement flow channel and through which blood can be introduced from a top side of the base;
a communication opening which is provided on another end side of the measurement flow channel and through which suction or pressure application with respect to air in the measurement flow channel or the blood introduced from the inlet into the measurement flow channel can be performed;
a moving body that is arranged in the measurement flow channel and that can move in the measurement flow channel;
a clotting accelerator applied on at least one of a flow channel wall surface, which defines the measurement flow channel, and the moving body;
a detection area through which light can be transmitted with respect to a predetermined part in the measurement flow channel and in which the moving body or the blood can be detected with light whether there is, in the predetermined part, the moving body or the blood making a reciprocating motion in the measurement flow channel in association with suction or pressure application of the air or the blood from the communication opening;
a cylindrical wall which has a cylindrical shape and is provided on a top surface side of the base;
an air chamber which is an inner space of the cylindrical wall and is connected to the communication opening;
a diaphragm which is provided on a top surface side of the cylindrical wall to close the air chamber and make the moving body and the blood make the reciprocating motion by applying pressure or reducing pressure with respect to the air chamber; and
a holder that has an annular shape and that is inserted into the cylindrical wall on an outer side in a radial direction of the cylindrical wall,
wherein the diaphragm is sandwiched between the cylindrical wall and the holder.
2. The blood clotting time measurement cartridge according to claim 1, wherein the measurement flow channel includes a narrowed part in a vicinity of the detection area.
3. The blood clotting time measurement cartridge according to claim 1, further comprising, on an outer side of the inlet, a shielding part that prevents the blood from flowing toward the detection area.
4. A blood clotting time measurement cartridge comprising:
a base;
a measurement flow channel provided on a bottom side of the base and extended long with respect to a cross-sectional area;
an inlet which is provided on one end side of the measurement flow channel and through which blood can be introduced from a top side of the base;
a communication opening which is provided on another end side of the measurement flow channel and through which suction or pressure application with respect to air in the measurement flow channel or the blood introduced from the inlet into the measurement flow channel can be performed;

a storage chamber that is connected to the communication opening and that stores the blood flowing out of the communication opening;

a stirring bar formed from a magnet or a ferromagnetic body that is arranged in the storage chamber and that stirs the blood in the storage chamber;

a clotting accelerator applied on at least one of a flow channel wall surface that defines the measurement flow channel, a storage chamber wall surface that defines the storage chamber, and the stirring bar; and a detection area through which light can be transmitted with respect to a predetermined part in the measurement flow channel and in which the blood can be detected with light whether there is, in the predetermined part, the blood making a reciprocating motion in the measurement flow channel in association with suction or pressure application of the air or the blood from the communication opening, wherein the stirring bar does not move to an outer side of the storage chamber.

5. The blood clotting time measurement cartridge according to claim 4, wherein the measurement flow channel includes a narrowed part in a vicinity of the detection area.

6. The blood clotting time measurement cartridge according to claim 4, further comprising, on an outer side of the inlet, a shielding part that prevents the blood from flowing toward the detection area.

7. The blood clotting time measurement cartridge according to claim 4, further comprising an air chamber connected to the storage chamber, and a diaphragm that closes the air chamber and makes the blood make a reciprocating motion in the measurement flow channel by applying pressure or reducing pressure with respect to the air chamber.

8. A blood clotting time measurement cartridge comprising:

a measurement flow channel in which blood is housed;

an inlet which is provided on one end side of the measurement flow channel and through which the blood is introduced into the measurement flow channel;

a communication opening which is provided on another end side of the measurement flow channel and through which suction or pressure application with respect to air in the measurement flow channel or the blood introduced from the inlet into the measurement flow channel can be performed; and a detection area through which light can be transmitted with respect to a predetermined part in the measurement flow channel and in which the blood is detected with light whether there is, in the predetermined part, the blood making a reciprocating motion in the measurement flow channel in association with suction or pressure application of the air or the blood in the measurement flow channel from the communication opening, wherein the measurement flow channel includes a helical flow channel in at least a part thereof, the helical flow channel is defined between a wall surface of a groove part that connects the inlet and the communication opening, and an outer peripheral surface of a shaft-like member that is housed in the groove part and that has a helical groove part winding in a helical manner in a surface, and the groove part has a pair of protruded parts that forms a narrowed part, in which the measurement flow channel is narrowed down, by being protruded from the wall surface of the groove part and that is placed in a vicinity of the detection area with the shaft-like member therebetween.

9. The blood clotting time measurement cartridge according to claim 8, wherein at least one of the protruded parts has an inclination surface on an opposite side of a side facing the shaft-like member.

10. A blood clotting time measuring device in which the blood clotting time measurement cartridge according to claim 8 is set, the device comprising:

a detection means that is provided in a position corresponding to the detection area and that can detect the blood with light.

11. The blood clotting time measurement cartridge according to claim 1, wherein the measurement flow channel comprises a pair of narrowed parts in a vicinity of the detection area.

12. The blood clotting time measurement cartridge according to claim 11, wherein the moving body moves only between the pair of narrowed parts.

13. The blood clotting time measurement cartridge according to claim 1, wherein a volume of the air chamber is adjusted by applying or releasing a pressure to the diaphragm.

14. The blood clotting time measurement cartridge according to claim 1, wherein the clotting accelerator is applied on the moving body.

15. The blood clotting time measurement cartridge according to claim 8, wherein an outer diameter of the shaft-like member is larger than an inner diameter of the narrowed part.

* * * * *